United States Patent
Verin et al.

(10) Patent No.: US 6,258,019 B1
(45) Date of Patent: Jul. 10, 2001

(54) CATHETER FOR INTRALUMINAL TREATMENT OF A VESSEL SEGMENT WITH IONIZING RADIATION

(75) Inventors: Vitali Verin; Youri Popowski, both of Geneva; Michael Schwager, Winterthur; Cirillo Ghielmetti, Koniz, all of (CH)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/391,433

(22) Filed: Sep. 8, 1999

Related U.S. Application Data

(63) Continuation-in-part of application No. 09/034,238, filed on Mar. 4, 1998, now abandoned, and a continuation-in-part of application No. 09/034,245, filed on Mar. 4, 1998, now abandoned.

(30) Foreign Application Priority Data

Sep. 26, 1997 (EP) .................................................. 97202957
Sep. 26, 1997 (EP) .................................................. 97202958

(51) Int. Cl.$^7$ ............................. A61N 5/00; A61M 29/00
(52) U.S. Cl. .................................. 600/1; 600/3; 606/194
(58) Field of Search .................................. 606/194, 195, 606/191, 192; 600/1–8

(56) References Cited

U.S. PATENT DOCUMENTS

| | | |
|---|---|---|
| 2,546,761 | 3/1951 | Loftus . |
| 2,862,108 | 11/1958 | Meilink . |
| 2,955,208 | 10/1960 | Stevens . |
| 3,060,924 | 10/1962 | Rush . |
| 3,147,383 | 9/1964 | Prest . |

(List continued on next page.)

FOREIGN PATENT DOCUMENTS

| | | |
|---|---|---|
| 2166915 A | 8/1996 | (CA) . |
| 91 02 312.2 | 8/1992 | (DE) . |
| 195 26 680 A1 | 1/1997 | (DE) . |

(List continued on next page.)

OTHER PUBLICATIONS

Tjho–Heslinga et al., "Results of ruthenium irradiation of uveal melanona", *Radiothereapy Oncology*, vol. 29, pp 33–38, 1993.

Lommatzsch et al., "Radiation effects on the optic nerve observed after brachytherapy of choroidal melanomas with 106Ru/106Rh plaques", *Graefe's Arch. Clin. Exp. Ophthalmology* vol. 232,pp. 482–487, 1994.

(List continued on next page.)

*Primary Examiner*—Samuel G. Gilbert
(74) *Attorney, Agent, or Firm*—Crompton, Seager & Tufte, LLC.

(57) ABSTRACT

A prepared catheter for intraluminal treatment of a vessel section with ionizing radiation, which catheter has an elongate shaft with a proximal end and distal end as percutaneous transluminal access to the vessel section, an inflatable balloon at the distal end of the shaft, and inflation lumen which runs through the shaft and opens into the balloon, and a source of ionizing radiation which can be positioned in the balloon, and which catheter is filled with a gas for applying pressure to the balloon. In this way, only a comparatively small proportion of the ionizing radiation is absorbed and rendered ineffective as it passes through the gas, and the intended dose of radiation can be administered within a short treatment time. The inflation lumen preferably has, along the greater part of the length lying within the patient's body during treatment, a cross-sectional area having a value in mm$^2$ not greater than the balloon in mm$^3$ divided by 1200. In this way, a reduction in the overall profile of the catheter is achieved while at the same time retaining the desired deflation times for the balloon.

7 Claims, 1 Drawing Sheet

U.S. PATENT DOCUMENTS

| | | |
|---|---|---|
| 3,324,847 | 6/1967 | Zoumboulis . |
| 3,505,991 | 4/1970 | Hellerstein et al. . |
| 3,643,096 | 2/1972 | Jeffries, Jr. et al. . |
| 3,669,093 | 6/1972 | Sauerwein et al. . |
| 3,674,006 | 7/1972 | Holmer . |
| 3,750,653 | 8/1973 | Simon . |
| 3,811,426 | 5/1974 | Culver et al. . |
| 3,861,380 | 1/1975 | Chassagne et al. . |
| 3,866,050 | 2/1975 | Whitfield . |
| 3,927,325 | 12/1975 | Hungate et al. . |
| 4,096,862 | 6/1978 | DeLuca . |
| 4,220,864 | 9/1980 | Sauerwein et al. . |
| 4,225,790 | 9/1980 | Parsons, Jr. et al. . |
| 4,244,357 | 1/1981 | Morrison . |
| 4,281,252 | 7/1981 | Parsons, Jr. et al. . |
| 4,314,157 | 2/1982 | Gaines . |
| 4,364,376 | 12/1982 | Bigham . |
| 4,584,991 | 4/1986 | Tokita et al. . |
| 4,588,395 | 5/1986 | Lemelson . |
| 4,631,415 | 12/1986 | Sauerwein et al. . |
| 4,702,228 | 10/1987 | Russell, Jr. et al. . |
| 4,706,652 | 11/1987 | Horowitz . |
| 4,763,642 | 8/1988 | Horowitz . |
| 4,763,671 | 8/1988 | Goffinet . |
| 4,782,834 | 11/1988 | Maguire et al. . |
| 4,784,116 | 11/1988 | Russell, Jr. et al. . |
| 4,815,449 | 3/1989 | Horowitz . |
| 4,819,618 | 4/1989 | Liprie . |
| 4,851,694 | 7/1989 | Rague et al. . |
| 4,861,520 | 8/1989 | van't Hooft et al. . |
| 4,881,937 | 11/1989 | van't Hooft et al. . |
| 4,897,076 | 1/1990 | Puthawala et al. . |
| 4,936,823 | 6/1990 | Colvin et al. . |
| 4,963,128 | 10/1990 | Daniel et al. . |
| 4,969,863 | 11/1990 | van't Hooft et al. . |
| 4,976,266 | 12/1990 | Huffman et al. . |
| 4,976,680 | 12/1990 | Hayman et al. . |
| 4,976,690 | 12/1990 | Solar et al. . |
| 5,030,194 | 7/1991 | Van't Hooft . |
| 5,032,113 | 7/1991 | Burns . |
| 5,059,166 | 10/1991 | Fischell et al. . |
| 5,084,001 | 1/1992 | Van't Hooft et al. . |
| 5,084,002 | 1/1992 | Liprie . |
| 5,092,834 | 3/1992 | Bradshaw et al. . |
| 5,103,395 | 4/1992 | Spako et al. . |
| 5,106,360 | 4/1992 | Ishiwara et al. . |
| 5,120,973 | 6/1992 | Rohe et al. . |
| 5,139,473 | 8/1992 | Bradshaw et al. . |
| 5,141,487 | 8/1992 | Liprie . |
| 5,147,282 | 9/1992 | Kan . |
| 5,163,896 | 11/1992 | Suthanthiran et al. . |
| 5,176,617 | 1/1993 | Fischell et al. . |
| 5,183,455 | 2/1993 | Hayman et al. . |
| 5,199,939 | 4/1993 | Dake et al. . |
| 5,213,561 | 5/1993 | Weinstein et al. . |
| 5,261,879 | 11/1993 | Brill . |
| 5,267,960 | 12/1993 | Hayman et al. . |
| 5,282,781 | 2/1994 | Liprie . |
| 5,302,168 | 4/1994 | Hess . |
| 5,344,383 | 9/1994 | Liping . |
| 5,354,257 | 10/1994 | Roubin et al. . |
| 5,370,685 | 12/1994 | Stevens . |
| 5,391,139 | 2/1995 | Edmundson . |
| 5,395,300 | 3/1995 | Liprie . |
| 5,405,309 | 4/1995 | Carden, Jr. . |
| 5,409,015 | 4/1995 | Palermo . |
| 5,411,466 | 5/1995 | Hess . |
| 5,425,720 | 6/1995 | Rogalsky et al. . |
| 5,429,582 | 7/1995 | Williams . |
| 5,484,384 | 1/1996 | Fearnot . |
| 5,498,227 | 3/1996 | Mawad . |
| 5,503,613 | 4/1996 | Weinberger . |
| 5,503,614 | 4/1996 | Liprie . |
| 5,532,122 | 7/1996 | Drukier . |
| 5,538,494 | 7/1996 | Matsuda . |
| 5,540,659 | 7/1996 | Teirstein . |
| 5,556,389 | 9/1996 | Liprie . |
| 5,575,749 | 11/1996 | Liprie . |
| 5,575,771 | 11/1996 | Walinsky . |
| 5,605,530 | 2/1997 | Fischell et al. . |
| 5,611,767 | 3/1997 | Williams . |
| 5,616,114 | 4/1997 | Thornton et al. . |
| 5,618,266 | 4/1997 | Liprie . |
| 5,624,372 | 4/1997 | Liprie . |
| 5,643,171 | 7/1997 | Bradshaw et al. . |
| 5,649,924 | 7/1997 | Everett et al. . |
| 5,653,683 | 8/1997 | D'Andrea . |
| 5,662,580 | 9/1997 | Bradshaw et al. . |
| 5,674,177 | 10/1997 | Hehrlein et al. . |
| 5,683,345 | 11/1997 | Waksman et al. . |
| 5,688,220 | 11/1997 | Verin et al. . |
| 5,707,332 | 1/1998 | Weinberger . |
| 5,713,828 | 2/1998 | Coniglione . |
| 5,720,717 | 2/1998 | D'Andrea . |
| 5,722,984 | 3/1998 | Fischell et al. . |
| 5,728,042 | 3/1998 | Schwager . |
| 5,730,698 | 3/1998 | Fischell et al. . |
| 5,776,099 | 7/1998 | Tremulis . |
| 5,782,740 | 7/1998 | Schneiderman . |
| 5,782,742 | 7/1998 | Crocker et al. . |
| 5,795,286 | 8/1998 | Fischell et al. . |
| 5,800,333 | 9/1998 | Liprie . |
| 5,803,895 | 9/1998 | Kronholz et al. . |
| 5,807,231 | 9/1998 | Liprie . |
| 5,816,259 | 10/1998 | Rose . |
| 5,816,999 | 10/1998 | Bischoff et al. . |
| 5,820,553 | 10/1998 | Hughes . |
| 5,833,593 | 11/1998 | Liprie . |
| 5,840,008 | 11/1998 | Klein et al. . |
| 5,840,009 | 11/1998 | Fischell et al. . |
| 5,840,064 | 11/1998 | Liprie . |
| 5,843,163 | 12/1998 | Wall . |
| 5,851,171 | 12/1998 | Gasson . |
| 5,851,172 | 12/1998 | Bueche et al. . |
| 5,855,546 | * 1/1999 | Hastings et al. ......................... 600/3 |
| 5,857,956 | 1/1999 | Liprie . |
| 5,863,284 | 1/1999 | Klein . |
| 5,863,285 | 1/1999 | Coletti . |
| 5,865,720 | 2/1999 | Hastings et al. . |
| 5,871,436 | 2/1999 | Eury . |
| 5,871,437 | 2/1999 | Alt . |
| 5,873,811 | 2/1999 | Wang et al. . |
| 5,879,282 | 3/1999 | Fischell et al. . |
| 5,882,290 | 3/1999 | Kume . |
| 5,882,291 | 3/1999 | Bradshaw et al. . |
| 5,891,091 | 4/1999 | Teirstein . |
| 5,897,573 | 4/1999 | Rosenthal et al. . |
| 5,899,882 | 5/1999 | Waksman et al. . |
| 5,906,573 | 5/1999 | Aretz . |
| 5,910,101 | * 6/1999 | Andrews et al. ......................... 600/3 |
| 5,910,102 | 6/1999 | Hastings . |
| 5,913,813 | 6/1999 | Williams et al. . |
| 5,916,143 | 6/1999 | Apple et al. . |
| 5,919,126 | 7/1999 | Armini . |
| 5,924,973 | 7/1999 | Weinberger . |
| 5,924,974 | 7/1999 | Loffler . |
| 5,938,582 | 8/1999 | Ciamacco, Jr. et al. . |
| 5,947,899 | 9/1999 | Hehrlein . |
| 5,947,924 | 9/1999 | Liprie . |
| 5,947,958 | 9/1999 | Woodard et al. . |
| 5,957,829 | 9/1999 | Thornton . |

| | | |
|---|---|---|
| 5,961,439 | 10/1999 | Chernomorsky et al. . |
| 5,967,966 | 10/1999 | Kronholz et al. . |
| 5,971,909 | 10/1999 | Bradshaw et al. . |
| 5,976,106 | 11/1999 | Verin et al. . |
| 5,997,462 | 12/1999 | Loffler . |
| 5,997,463 | 12/1999 | Cutrer . |
| 6,010,445 | 1/2000 | Armini et al. . |
| 6,013,019 | 1/2000 | Fischell et al. . |
| 6,013,020 | 1/2000 | Meloul et al. . |
| 6,024,690 | 2/2000 | Lee et al. . |
| 6,030,333 | 2/2000 | Sioshansi et al. . |
| 6,033,357 | 3/2000 | Ciezki et al. . |
| 6,099,454 * | 8/2000 | Hastings et al. ............ 600/3 |

FOREIGN PATENT DOCUMENTS

| | | |
|---|---|---|
| 197 54 870 A1 | 8/1998 | (DE) . |
| 197 24 233 C1 | 12/1998 | (DE) . |
| 197 58 234 | 7/1999 | (DE) . |
| 198 07 727 | 7/1999 | (DE) . |
| 198 25 563 | 12/1999 | (DE) . |
| 198 25 999 | 12/1999 | (DE) . |
| 198 26 000 | 12/1999 | (DE) . |
| 198 29 447 | 1/2000 | (DE) . |
| 0 360 582 | 8/1990 | (EP) . |
| 0 514 913 A2 | 11/1992 | (EP) . |
| 0 633 041 A1 | 1/1995 | (EP) . |
| 0 686 342 A1 | 12/1995 | (EP) . |
| 0 688 580 A1 | 12/1995 | (EP) . |
| 0 696 906 B1 | 2/1996 | (EP) . |
| 0 749 764 A1 | 12/1996 | (EP) . |
| 0 754 472 A2 | 1/1997 | (EP) . |
| 0 754 473 A2 | 1/1997 | (EP) . |
| 0 593 136 B1 | 3/1997 | (EP) . |
| 0 778 051 A1 | 6/1997 | (EP) . |
| 0 801 961 A2 | 10/1997 | (EP) . |
| 0 810 004 | 12/1997 | (EP) . |
| 0 813 894 A2 | 12/1997 | (EP) . |
| 0 629 380 B1 | 7/1998 | (EP) . |
| 0 865 803 | 9/1998 | (EP) . |
| 0 904 798 | 3/1999 | (EP) . |
| 0 904 799 | 3/1999 | (EP) . |
| 10071210 | 3/1998 | (JP) . |
| WO 86/03124 | 6/1986 | (WO) . |
| WO 93/04735 | 3/1993 | (WO) . |
| WO 94/25106 | 11/1994 | (WO) . |
| WO 94/26205 | 11/1994 | (WO) . |
| WO 95/07732 | 3/1995 | (WO) . |
| WO 96/06654 | 3/1996 | (WO) . |
| WO 96/10436 | 4/1996 | (WO) . |
| WO 96/13303 | 5/1996 | (WO) . |
| WO 96/14898 | 5/1996 | (WO) . |
| WO 96/17654 | 6/1996 | (WO) . |
| WO 96/22121 | 7/1996 | (WO) . |
| WO 96/29943 | 10/1996 | (WO) . |
| WO 96/40352 | 12/1996 | (WO) . |
| WO 97/07740 | 3/1997 | (WO) . |
| WO 97/09937 | 3/1997 | (WO) . |
| WO 97/17029 | 5/1997 | (WO) . |
| WO 97/18012 | 5/1997 | (WO) . |
| WO 97/19706 | 6/1997 | (WO) . |
| WO 97/25102 | 7/1997 | (WO) . |
| WO 97/25103 | 7/1997 | (WO) . |
| WO 97/40889 | 11/1997 | (WO) . |
| WO 98/01183 | 1/1998 | (WO) . |
| WO 98/01184 | 1/1998 | (WO) . |
| WO 98/01185 | 1/1998 | (WO) . |
| WO 98/01186 | 1/1998 | (WO) . |
| WO 98/11936 | 3/1998 | (WO) . |
| WO 98/16151 | 4/1998 | (WO) . |
| WO 98/20935 | 5/1998 | (WO) . |
| WO 98/25674 | 6/1998 | (WO) . |
| WO 98/29049 | 7/1998 | (WO) . |
| WO 98/30273 | 7/1998 | (WO) . |
| WO 98/34681 | 8/1998 | (WO) . |
| WO 98/36788 | 8/1998 | (WO) . |
| WO 98/36790 | 8/1998 | (WO) . |
| WO 98/36796 | 8/1998 | (WO) . |
| WO 98/39052 | 9/1998 | (WO) . |
| WO 98/39062 | 9/1998 | (WO) . |
| WO 98/39063 | 9/1998 | (WO) . |
| WO 98/40032 | 9/1998 | (WO) . |
| WO 98/46309 | 10/1998 | (WO) . |
| WO 98/55179 | 12/1998 | (WO) . |
| WO 98/57706 | 12/1998 | (WO) . |
| WO 99/01179 | 1/1999 | (WO) . |
| WO 99/02219 | 1/1999 | (WO) . |
| WO 99/04706 | 2/1999 | (WO) . |
| WO 99/04856 | 2/1999 | (WO) . |
| WO 99/10045 | 3/1999 | (WO) . |
| WO 99/21615 | 5/1999 | (WO) . |
| WO 99/21616 | 5/1999 | (WO) . |
| WO 99/22774 | 5/1999 | (WO) . |
| WO 99/22775 | 5/1999 | (WO) . |
| WO 99/22812 | 5/1999 | (WO) . |
| WO 99/22815 | 5/1999 | (WO) . |
| WO 99/24116 | 5/1999 | (WO) . |
| WO 99/24117 | 5/1999 | (WO) . |
| WO 99/29354 | 6/1999 | (WO) . |
| WO 99/29370 | 6/1999 | (WO) . |
| WO 99/29371 | 6/1999 | (WO) . |
| WO 99/30779 | 6/1999 | (WO) . |
| WO 99/34969 | 7/1999 | (WO) . |
| WO 99/36121 | 7/1999 | (WO) . |
| WO 99/39628 | 8/1999 | (WO) . |
| WO 99/40962 | 8/1999 | (WO) . |
| WO 99/40970 | 8/1999 | (WO) . |
| WO 99/40971 | 8/1999 | (WO) . |
| WO 99/40972 | 8/1999 | (WO) . |
| WO 99/40973 | 8/1999 | (WO) . |
| WO 99/40974 | 8/1999 | (WO) . |
| WO 99/42162 | 8/1999 | (WO) . |
| WO 99/42163 | 8/1999 | (WO) . |
| WO 99/42177 | 8/1999 | (WO) . |
| WO 99/44686 | 9/1999 | (WO) . |
| WO 99/44687 | 9/1999 | (WO) . |
| WO 99/49935 | 10/1999 | (WO) . |
| WO 99/56825 | 11/1999 | (WO) . |
| WO 99/56828 | 11/1999 | (WO) . |
| WO 99/61107 | 12/1999 | (WO) . |
| WO 99/62598 | 12/1999 | (WO) . |
| WO 99/66979 | 12/1999 | (WO) . |
| WO 00/03292 | 1/2000 | (WO) . |
| WO 00/04838 | 2/2000 | (WO) . |
| WO 00/04953 | 2/2000 | (WO) . |
| WO 00/09212 | 2/2000 | (WO) . |

OTHER PUBLICATIONS

*Radiotherapy of Intraoculare and Orbital Tumors*, Springer–Verlak publishers, Berlin Heidelberg and New York, copyright 1993, pp. 23–30 and 363–367.

Fackelmann, "Harbinger of a Heart Attack", *Science News*, vol. 151, Jun. 14, 1997, pp. 374–375.

Raloff, "Nuclear Medicine Gets Friendlier—Experimental Therapies Seek to Poison Just the Disease", *Science News*, vol. 152, Jul. 19, 1997, pp. 40–41.

Sutherland, "Managing Cancer Through Synergy", *Administrative Radiology Journal*, Nov. 1996, pp. 21–27.

* cited by examiner

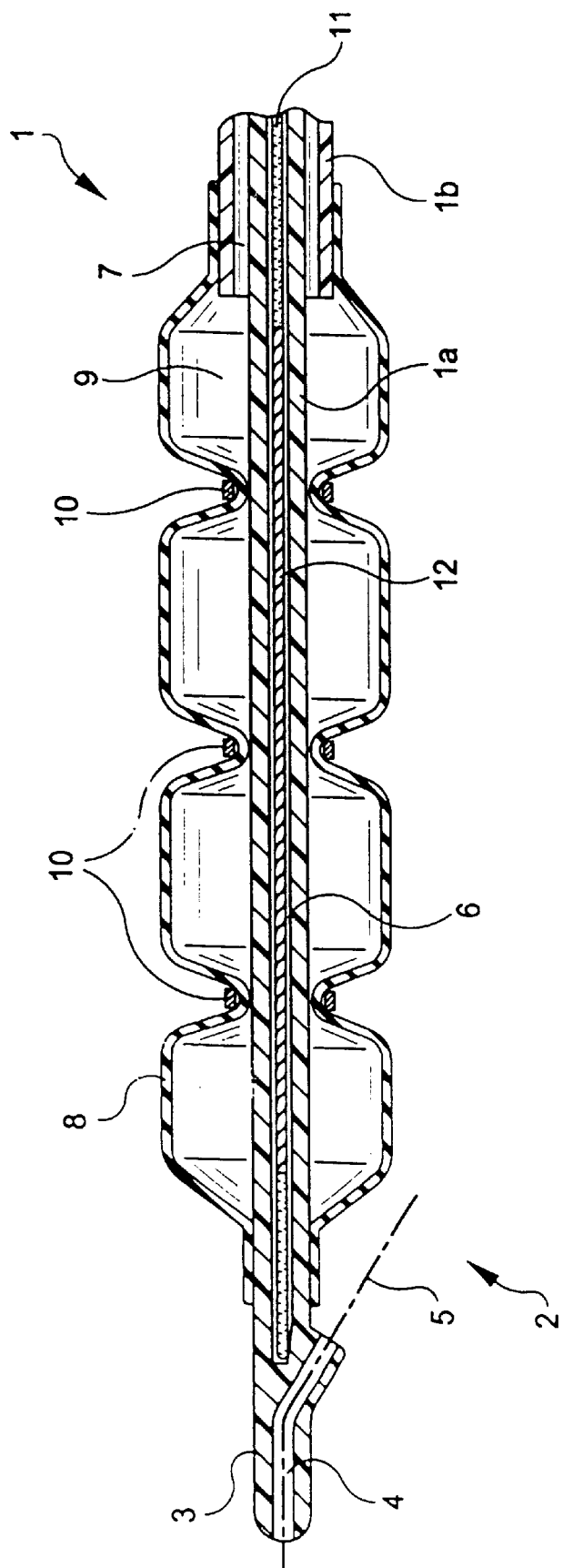

CATHETER FOR INTRALUMINAL TREATMENT OF A VESSEL SEGMENT WITH IONIZING RADIATION

CROSS REFERENCE TO RELATED APPLSICATION

This application is a continuation-in-part of co-pending U.S. Patent Application entitled CATHETER FOR INTRALUMINAL TREATMENT OF A VESSEL SEGMENT WITH IONIZING RADIATION Ser. No. 09/034,238 filed Mar. 4, 1998, now abandoned which claims priority under 35 U.S.C. §119 to European Patent Application No. 97202957.3, filed in the European Patent Office on Sep. 26, 1997, the entire disclosure of which is hereby incorporated by reference.

This application is also a continuation-in-part of co-pending U.S. Patent Application entitled BALLOON CATHETER WITH LOW VISCOSITY INFLATION FLUID Ser. No. 09/034,245 filed Mar. 4, 1998, now abandoned which claims priority under 35 U.S.C. §119 to European Patent Application No. 97202958.1, filed in the European Patent Office on Sep. 26, 1997, the entire disclosure of which is hereby incorporated by reference.

FIELD OF THE INVENTION

The invention relates to prepared catheters for intraluminal treatment of a vessel section with ionizing radiation. In particular, the invention relates to prepared balloon catheters for such use.

BACKGROUND OF THE INVENTION

Catheters for intraluminal treatment of a vessel section with ionizing radiation are used, for example, during or after percutaneous transluminal angioplasty, such as balloon dilatation or atherectomy of a stenosed blood vessel section, in order to prevent restenosis of this section. This is based on the theory that application of a defined dose of ionizing radiation can inhibit excessive cell proliferation triggered by the angioplasty and that by this means, restenosis of the treated vessel section can be avoided. A catheter of the generic type, however, can also be used for radiation treatment of other body cavities such as the esophagus or trachea or for treatment of the prostate.

A balloon catheter of the type mentioned in the introduction is known from EP 633,041 A1, in which a guide wire is arranged to be longitudinally displaceable in a central guide wire lumen of a two-lumen balloon catheter. An emitter of radioactive radiation in the form of a filament is incorporated into the tip of the guide wire. The second lumen serves as an inflation lumen for the balloon. Inflation of the balloon serves to radially center the radiation emitter positioned in the guide wire lumen in the vessel section that is to be treated. In this way, a radiation dose distribution is obtained uniformly about the circumference of the vessel wall. For applying the pressure to the balloon, a conventional liquid solution is used. The radiation source preferably used is yttrium-90, an easily screenable beta emitter with a half-life of 2.7 days, a mean electron energy of 0.942 MeV and a maximum electron energy of 2.28 MeV.

Over the greater part of its course from the emitter positioned in the balloon to the vessel wall to be treated, the radioactive radiation has to pass through inflation medium, in which process—as in any matter—radiation energy is absorbed. Thus, the energy dose available at the surface of the vessel wall, and the depth of penetration of the radiation into the vascular tissue at the wall, depend on the initial activity of the source, on the coefficient of absorption of the inflation medium, and on the length of travel of the radiation through the inflation medium.

The conventional liquid solution used to inflate the balloon includes saline and radiopaque contrast media which have a significant coefficient of absorption. Thus, known catheters of the type mentioned in the introduction suffer the drawback of long irradiation times, and consequently, long treatment times. Because of the necessary centering of the emitter in an inflated balloon, the flow of blood in the treated vessel has to be interrupted during this long treatment, which is undesirable.

The increasing importance of minimally invasive surgery and the treatment of ever narrower blood vessels demand guide catheters, and consequently balloon catheters, of ever smaller profile. Flexibility as well as longitudinal force and torsion transmission of the guide wire, balloon catheter and guide catheter must be guaranteed, as well as low friction between guide wire and balloon catheter. An adequately short deflation time for the balloon and a sufficiently large annular lumen for the flow of contrast medium are also necessary. If the inflation lumen is too narrow, the inflation medium can no longer flow quickly enough out of the balloon. A catheter with slow emptying of the balloon blocks the bloodstream for longer and thus, for example, also precludes the possibility of responding quickly to an ischemic reaction on the part of the patient during treatment.

SUMMARY OF THE INVENTION

The invention is therefore based on the object of providing a balloon catheter, in which as small a proportion as possible of the ionizing radiation is absorbed on its travel from the source through the inflated balloon to the vessel section that is to be treated. It is also based on the object of providing a balloon catheter which has short deflation times and has a small overall profile.

According to a first embodiment of the invention, the object is achieved by means of a balloon catheter inflated with a gas, as opposed to a conventional liquid. When the inflation medium is a gas, the radiation passes through a medium with a comparatively low coefficient of absorption, since the latter is generally higher for liquids than it is for gases. Therefore, the radiation attenuates only slightly as it passes through the inflation medium, so that a sufficient radiation dose can be delivered to the vessel section within a short time. In addition, the radiation intensity is less dependent on the source distance, as a result of which inaccuracies in the centering of the source have only slight effects on the uniformity of the dose distribution.

Furthermore, gas-filled balloons have up to about three times shorter deflation times compared to balloons which have been inflated with liquid, a fact which is attributable to the lower viscosity of gases compared to liquids. The advantage of this is, for example, that when providing treatment using a balloon which interrupts the flow of blood, it is possible to respond quickly to an ischaemic reaction on the part of the patient by deflating the balloon.

Further yet, when the inflation medium used is a gas (i.e., a lower viscosity than the conventional inflation liquid media), it is possible, while having essentially the same deflation time, for the inflation lumen to be made smaller in cross-section along the greater part of its length running within the patient during treatment, with greater advantages for all other properties of the catheter. For example, as a result of the smaller overall profile, the flow of contrast medium is improved, while at the same time, however, the flexibility and the kink resistance are also improved, since with smaller shaft diameters the wall thickness can be reduced. The reduction in cross-section which can be achieved by means of the invention can either be specified in absolute values, as specified in the claims, or, as specified in other claims, as a function of the maximum use volume of the balloon which has to be deflated.

In a preferred embodiment of the invention, the inflation medium is carbon dioxide. In the treatment of blood vessels, it is possible, in the event of a leaking or defective balloon, for the blood to absorb a certain amount of carbon dioxide without harming the patient. Since carbon dioxide is transported anyway in the blood, its biological tolerability in humans is not in question.

In a further advantageous embodiment of the invention, the inflation lumen has, along the greater part of its length lying within the patient's body during treatment, a cross-sectional area of at most $0.300$ mm$^2$, or at most $0.200$ mm$^2$. The cross-sectional area of the inflation lumen can also be defined as a function of the balloon volume, for example when expressed in mm$^2$, not greater than a maximum use volume of the balloon in mm$^3$ divided by 1200 or 1600. By reducing the cross-sectional area of the inflation lumen, the overall profile of the catheter can be made smaller, as a result of which a catheter according to the invention is suitable for minimally invasive percutaneous transluminal treatments via small puncture openings and guide catheters. In addition, the catheter can also be used in correspondingly narrower vessels, in which case the time for the balloon to empty still remains small compared to known catheters with liquid inflation media.

In sum the present invention relates to a catheter for intraluminal treatment of a vessel section, which catheter has an elongate shaft with a proximal end and a distal end, a balloon which is arranged at the distal end of the shaft and can be inflated to a maximum use volume, and an inflation lumen which runs through the shaft and opens into the balloon, and which catheter is filled with an inflation medium for applying pressure to the balloon. The inflation medium has a viscosity which is lower than that of water. The inflation lumen may have along the greater part of the length lying within the patient's body during treatment a cross-sectional area having a value in mm$^2$ not greater than the maximum use volume of the balloon in mm$^3$ divided by 1200, optionally not greater than the maximum use volume of the balloon in mm$^3$ divided by 1600. The inflation lumen may have along the greater part of the length lying within the patient's body during treatment a cross-sectional area of at most $0.300$ mm$^2$, optionally at most $0.200$ mm$^2$. The inflation medium may be a gas, preferably carbon dioxide.

Further properties of a catheter according to the invention will become apparent from an illustrative embodiment which is described in detail hereinbelow with reference to the drawing. This example involves a catheter for intraluminal treatment of a vessel section with ionizing radiation. Controlled deflation times, with a small shaft cross-section, are of particular interest here. In the case of protracted irradiation times, as can result from the abating energy of the emitter, the burden on the patient is minimized by interrupting the flow of blood. The advantages of the invention are seen not only in this application, however, but in all balloon catheters whose deflation time and whose overall profile are of interest, such as in the case of the catheters mentioned in the introduction, in the case of dilation catheters or occlusion catheters for use in coronary or peripheral blood vessels or in neurology, and in the case of other catheters.

BRIEF DESCRIPTION OF THE DRAWING

Further advantages of a catheter according to the invention will become apparent from a preferred illustrative embodiment which is described in detail hereinbelow with reference to the drawing, in which:

FIG. 1 shows, in a longitudinal cutaway, the distal section of a catheter according to the invention.

DETAILED DESCRIPTION OF THE INVENTION

According to FIG. 1, a catheter according to the invention for intraluminal treatment of a vessel section with ionizing radiation has a three-lumen shaft 1 which has a proximal end (not shown) and a distal end 2, and serves as transluminal access to the vessel section. The shaft 1 is made up of an outer shaft 1b and an inner shaft 1a which runs coaxially inside the latter and projects distally from it. In a tip 3 of the inner shaft 1b there is a short guide wire lumen 4 for receiving a guide wire (not shown, course indicated by dot-and-dash line 5), onto which the catheter is threaded in order to be advanced through the vessel system. During the insertion of the catheter, a central lumen 6 which is closed distally is used for receiving a stiffening wire (not shown) which transmits axial thrust to the tip 3 as the shaft 1 is being advanced. An annular inflation lumen 7 running between inner shaft 1a and outer shaft 1b opens into a balloon 8 arranged at the distal end 2 of the shaft 1, which balloon 8 is filled, via the inflation lumen 7, with an inflation medium 9, for example carbon dioxide, and is thereby inflated. With approximately the same emptying time for the balloon 8, the use of carbon dioxide as inflation medium permits a reduction in the cross-sectional area of the inflation lumen 8, for example to values of less than $0.300$ mm$^2$, although cross-sectional areas of less than $0.200$ mm$^2$ have already been produced. The achievable ratio between the maximum use volume of the balloon and the cross-sectional area of the inflation lumen, with tolerable emptying times, is approximately 1200:1. In order to obtain a thin outer shaft 1b, the emptying times evolving from a ratio of 1600:1 have also been accepted in some cases. The inflated balloon 8 is subdivided into a plurality of balloon segments by constrictions which are formed by ring elements 10, as a result of which the central lumen 6 is radially centered even in the event of deformation of the inner shaft 1a. When the balloon catheter has been positioned, the stiffening wire is removed from the central lumen 6 and replaced by a source wire 11 into which a source 12 of ionizing radiation is incorporated distally. The source 12 is, for example, a filament of yttrium-90, which is positioned in the balloon is such a way that the emitted beta radiation substantially passes through the inflation medium 9 on its travel to the vessel wall.

The carbon dioxide used as inflation medium is, for example, kept ready in gas bottles at a pressure of 11 bar, for example. The gas pressure can be reduced via a reducing valve, so that an inflation syringe can also be filled with carbon dioxide in the sterile area of a catheter laboratory. Air is removed from the balloon and inflation lumen of the catheter in a customary manner, for instance with a syringe creating a vacuum. The balloon can thereafter be inflated with the carbon dioxide taken up by the inflation syringe.

The above-described embodiments of the invention are merely descriptive of its principles and are not to be considered limiting. Further modifications of the invention herein disclosed will occur to those skilled in the respective arts and all such modifications are deemed to be within the scope of the invention as defined by the modifications are deemed to be within the scope of the invention as defined by the following claims.

We claim:

1. A prepared balloon catheter for intraluminal ionizing radiation treatment of a vessel section within a patient's body, the catheter having an elongate shaft with a gas-filled inflation lumen extending therthrough, and a balloon disposed on a distal end of the shaft, the balloon having a maximum inflated volume, wherein the inflation lumen extending through the shaft has a cross-sectional area having a value in $mm^2$ not greater than the maximum inflated volume of the balloon in $mm^3$ divided by 1200.

2. A prepared balloon catheter for intraluminal ionizing radiation treatment of a vessel section within a patient's body, the catheter having an elongate shaft with a proximal end and a distal end, a balloon arranged at the distal end of the shaft, the balloon having a maximum inflated volume, and an inflation lumen having a length which runs through the shaft and opens into the balloon, wherein the catheter is filled with an inflation medium having a viscosity lower than that of water for applying pressure to the balloon, and wherein the inflation lumen has, along the greater part of the length lying within the patient's body during treatment, a cross-sectional area having a value in $mm^2$ not greater than the maximum inflated volume of the balloon in $mm^3$ divided by 1200.

3. The catheter of claim 2, wherein the inflation lumen has, along the greater part of the length lying within the patient's body during treatment, a cross-sectional area having a value in $mm^2$ not greater than the maximum inflated volume of the balloon in $mm^3$ divided by 1600.

4. The catheter of claim 2, wherein the inflation lumen has, along the greater part of the length lying within the patient's body during treatment, a cross-sectional area of at most 0.300 $mm^2$.

5. The catheter of claim 4, wherein the inflation lumen has, along the greater part of the length lying within the patient's body during treatment, a cross-sectional area of at most 0.200 $mm^2$.

6. The catheter of claim 2, wherein the inflation medium is a gas.

7. The catheter of claim 6, wherein the inflation medium is carbon dioxide.

* * * * *